United States Patent
Yoo (10) Patent No.: US 8,267,318 B2
(45) Date of Patent: Sep. 18, 2012

(54) LIQUID BARCODE AND LIQUID BARCODE READER

(75) Inventor: Jae Chern Yoo, Pohang-si (KR)

(73) Assignee: Samsung Electronic Co., Ltd., Suwon-Si (KR)

( * ) Notice: Subject to any disclaimer, the term of this patent is extended or adjusted under 35 U.S.C. 154(b) by 302 days.

(21) Appl. No.: 12/734,262

(22) PCT Filed: Oct. 21, 2008

(86) PCT No.: PCT/KR2008/006221
§ 371 (c)(1),
(2), (4) Date: Apr. 21, 2010

(87) PCT Pub. No.: WO2009/054664
PCT Pub. Date: Apr. 30, 2009

(65) Prior Publication Data
US 2010/0213255 A1    Aug. 26, 2010

(30) Foreign Application Priority Data

Oct. 23, 2007  (KR) .................. 10-2007-0107501

(51) Int. Cl.
*G06K 19/06* (2006.01)

(52) U.S. Cl. ........................ 235/449; 235/494

(58) Field of Classification Search .................. 235/449, 235/494, 462.01, 454, 375, 488
See application file for complete search history.

(56) References Cited

U.S. PATENT DOCUMENTS

| 5,733,739 | A | 3/1998 | Zakim et al. |
| 6,082,620 | A * | 7/2000 | Bone, Jr. ................. 235/462.16 |
| 7,028,906 | B2 * | 4/2006 | Challa et al. ............. 235/462.46 |
| 2001/0051714 | A1 | 12/2001 | Chen et al. |
| 2004/0121076 | A1 | 6/2004 | Haines |
| 2007/0187507 | A1 * | 8/2007 | Natsume et al. ........... 235/462.1 |
| 2008/0017700 | A1 * | 1/2008 | Kudo ............................ 235/375 |
| 2008/0149701 | A1 * | 6/2008 | Lane ............................. 235/375 |
| 2009/0102879 | A1 * | 4/2009 | Katada et al. .................. 347/17 |
| 2010/0072278 | A1 * | 3/2010 | Putnam et al. ................ 235/454 |
| 2011/0310461 | A1 * | 12/2011 | Bouchard et al. ............. 359/296 |

FOREIGN PATENT DOCUMENTS

JP     2003-222893     8/2003

OTHER PUBLICATIONS

European Search Report dated Oct. 7, 2010 in corresponding European Patent Application 08842656.4.
International Search Report for PCT/KR2008/006221, mailed Mar. 27, 2009.

* cited by examiner

*Primary Examiner* — Thien M Le
(74) *Attorney, Agent, or Firm* — Staas & Halsey LLP (57) ABSTRACT

The inventive concept relates to a product authentication and identification device using a liquid barcode formed by liquid bars stored in liquid chambers. For example, according to the inventive concept liquid barcodes and a liquid barcode reader for reading liquid barcodes used for product authentication and identification of thin-film chemical analyzers such as a lab-on-a-disc and a bio disc in which bio chips such as a lab-on-a-chip, a protein chip, and a DNA chip for diagnosing and detecting a small amount of material in a fluid are integrated, a credit card, or other products can be provided.

21 Claims, 8 Drawing Sheets

LIQUID BARCODE AND LIQUID BARCODE READER

CROSS REFERENCE TO RELATED APPLICATIONS

This application claims the benefit under 35 U.S.C. Section 371, of PCT International Application No. PCT/KR2008/006221, filed Oct. 21, 2008, which claimed priority to Korean Application No. 10-2007-0107501, filed Oct. 23, 2007, the disclosures of which are hereby incorporated by reference.

TECHNICAL FIELD

The inventive concept relates to a product authentication and identification device using a liquid barcode formed by liquid bars stored in liquid chambers.

BACKGROUND ART

A barcode includes a combination of white and black bar-shaped portions which represent a binary code. Barcodes are used to input data quickly and they are easy to read for a computer. A barcode may have a form that is automatically read by an optical mark reader connected to a computer and then, is input to the computer and stored or recognized. A barcode indicates a type of product complying with a universal product code (UPC), or is used for a point-of-sales (POS) system of sales information in supermarkets and the like. The price of a product corresponding to a barcode can be displayed separately on a display device. The barcode is encoded according to a standard such as the UPC, and then, is decoded through a reader formed with a barcode scanner and a decoder. If the scanner reads the barcode, the code is transferred to the decoder, and the code is decoded so that the code can be transformed into information that can be understood. Decoding of information in the barcode is performed by the scanner. A black bar that is a black bar portion of the barcode allows a small amount of light to be reflected to the scanner, while white space bars positioned between black bars reflect more light. The difference between amounts of reflected light can be translated into an electrical signal by a photo detector in the scanner, and the signal can be read.

In the reading of a barcode, hand held scanners were used in the past. More recently, laser-type scanners have been mainly used. In the laser type, a barcode is automatically read by moving a product on which the barcode is printed, across a reader such that the work can be made more efficient. In a factory automation field, a barcode is attached to an object to be processed so that it can help with the identifying of various items required for a job by recognizing a lot number and a product number. Also, a barcode can be used for a variety of purposes including sales information in a shop, and management of books, proof of identification and identification of products in a library. A barcode can be printed on a variety of materials in addition to paper, and has an advantage that desired information can be quickly accessed. However, since the capacity of information in the barcode is limited, the barcode has a drawback that not all types of information regarding a product can be fully known from the barcode. In order to compensate for this drawback, a 2-dimensional (2D) barcode, i.e., a matrix code, has been developed recently.

Though the 2D barcode does not have a big difference from the conventional barcodes, it can include more information because about 4,000 characters can be coded in a mosaic-type arrangement of black and white rectangles instead of the linear arrangement used in the conventional linear barcodes. However, these 2D barcodes have the following two problems. Firstly, the barcode can be copied such that reliability and accuracy of information obtained from the barcode is lowered. Secondly, the amount of information of all conventional barcodes, including the 2D barcodes, is limited because information is expressed in a binary code by white and block. Accordingly, in order to overcome these problems, an embodiment of the inventive concept provides a liquid barcode in which a series of a plurality of chambers are formed as bar-shaped liquid bars and arranged in parallel.

The conventional credit card adopts a magnetic recognition method. If a magnetic card such as a credit card is passed through an automatic teller machine (ATM) or a card reader by a user, magnetic information recorded in the card is transformed into an electrical signal. The signal is transferred into the inside of the reader, and is transformed into a predetermined binary code, thereby inputting information included in the card. For a magnetic card, a magnetic tape is attached to a PVC card such as an ordinary credit card, and then used. The magnetic recognition method is widely used because it allows recording of basic information and easy recording and deleting of additional information. However, the method has a problem that copying is possible.

DETAILED DESCRIPTION OF THE INVENTIVE CONCEPT

Technical Problem

The inventive concept provides liquid barcodes and a liquid barcode reader for reading the liquid barcodes which can be used for product authentication and identification of thin-film chemical analyzers such as a lab-on-a-disc and a bio disc in which bio chips such as a lab-on-a-chip, a protein chip, and a DNA chip for diagnosing and detecting a small amount of material in a fluid are integrated, a credit card, and other products.

Technical Solution

Hereinafter, the bar-shaped chamber will be referred to as a liquid bar.

According to an aspect of the inventive concept, there is provided a liquid barcode in which a series of liquid bars storing liquid are integrated in parallel in a plastic body. For example, according to an aspect of the inventive concept, there is provided a liquid barcode including: liquid bars formed of bar-shaped chambers filled with liquid; space bars formed in the gap spaces between the liquid bars; and a plastic body formed by arranging in parallel and integrating therein a plurality of the liquid bars and space bars. The plastic body may further selectively include a magnetic tape.

According to another aspect of the inventive concept, there is provided a liquid barcode reader including a spectrometer for reading a spectrometer reading optical characteristics of the plastic body in which the liquid barcode is integrated and the liquid barcode.

In the liquid barcode, the liquid bar may further include numerical information at the bottom or top of the bar. The numerical information may be a product item code, a manufacturer code or a country identification code.

The liquid bar of a quiet zone of the liquid barcode may store a background (blank) solution.

The liquid bar may be formed with a series of liquid bars including nanoparticles of different sizes. The liquid bar may be formed with a series of liquid bars including nanoparticles of different densities. The liquid bar may be formed with a series of liquid bars including nanoparticles of different 3-dimensional structures. The liquid barcode can include much information by a variety of combinations of the variety of liquids stored in each liquid bar, the widths of the liquid bars, the number of the liquid bars or the widths of the space bars.

The space between liquid bars may form a space bar. For example, gaps between liquid bars can form a space bar.

The plastic body may be formed by laminating a top substrate and a bottom substrate. The liquid barcode may be formed by a series of bar shapes engraved by the top substrate and/or the bottom substrate.

The top substrate of the plastic body may further include a reflection layer.

The plastic body may further include a magnetic tape.

According to another aspect of the inventive concept, there is provided a liquid barcode reader including a spectrometer reading optical characteristics of a liquid barcode; and a central processing unit (CPU) controlling the spectrometer, or driving a bio disc or a thin-film chemical analyzer.

The liquid barcode reader may further include a slit allowing light to enter therein and exit therefrom.

The liquid barcode reader may further include a magnetic card reader reading information of a magnetic tape.

The liquid in the liquid barcode may be transparent or may be opaque but transparent in a visible band.

The liquid barcode may be arranged in the thin-film chemical analyzer to provide product authentication and identification functions for the thin-film chemical analyzer.

The liquid barcode chambers and the magnetic tape may be arranged on the thin-film chemical analyzer so that liquid barcodes capable of storing product information on the thin-film chemical analyzer, storing analysis results and recording of additional information can be provided. For example, since the liquid barcode cannot be copied, it can be used for identification and authentication of a product of the thin-film chemical analyzer, and the magnetic tape can be used for storing product information for the thin-film chemical analyzer, storing analysis results, and recording of additional information.

The liquid barcode and the magnetic tape for the thin-film chemical analyzer may be arranged on an outer circumference of the thin-film chemical analyzer.

The plastic body may be in the form of an adhesive tape. In this case, the liquid barcode may be attached to a product which requires product identification and authentication.

The thin-film body may form part of a product or may be attached to a product so that a liquid barcode for deciding whether or not the product is genuine can be provided. The product may be a luxury handbag, an art work, a digital versatile disc (DVD), a bio disc, a thin-film chemical analyzer, a memory card, a credit card, an entrance card, or an expensive product.

The liquid stored in the liquid bar may include a liquid in a gel state. The thin-film chemical analyzer may include a bio disc integrating a thin-film analyzer or a lab-on-a-chip for diagnosing or detecting a small amount of a bio substance (sample) or a chemical substance in a fluid, such as a lab-on-a-chip to which an ELISA/CLISA analysis method is applied; a lab-on-a-chip to which a Rapid test method is applied; a lab-on-a-chip to which an immunological method is applied; a lab-on-a-chip to which a biochemical method is applied; or a lab-on-a-chip for examinations of food poisoning germs, remaining antibiotics, remaining agrichemicals, heavy metals in polluted water, genetically modified food, food allergies, polluted materials, germs such as coliforms and salmonellas, confirmation of biological children, types of meat, and identification of an origin. The examination of remaining agrichemicals may include examination of organophosphate and carbamate insecticides which are most widely used among agrichemicals for vegetables and fruits.

The bio materials (samples) may include one or more selected from among DNA, oligonucleotide, RNA, PNA, ligand, receptor, antigen, antibody, milk, urine, saliva, hair, crops and vegetable samples, meat samples, fish samples, bird samples, polluted water, domestic animal samples, food samples, food materials, stored food, mouth cells, tissue cells, saliva, semen, protein, or other biomass. The food materials are materials to prepare food, and may include, for example, food materials for stew, food materials for kimchi, and food materials for soup.

When urine is examined, the thin-film chemical analyzer may perform analyses of leucocyte, blood, protein, nitrile, pH, specific gravity, glucose, ketone, ascorbic acid, urobilinogen, and bilirubin. When hair is examined, the historical record by accumulation of nutrients and poisonous materials in a human body including minerals can be more accurately measured compared to blood or urine analyses. Also, excess and lack of inorganic materials in a long period can be accurately known, and it becomes a sample to find the amounts of poisonous heavy metals which is widely known to persons skilled in the art. The biochemical analysis may include analyses of GOT, GPT, ALP, LDH, GGT, CPK, amylase, T-protein, albumin, glucose, T-cholesterol, triglycerides, T-bilirubin, D-bilirubin, BUN, creatinine, I-phosphorus, calcium, and uric acid.

The rapid test method may include a strip in which many types of tumor markers or capture probes are fixed in the form of a line or spot on a porous membrane. The rapid test method and the ELISA method may include many types of tumor markers or capture probes fixed on the substrate in the form of a line or spot. The tumor markers may include one or more selected from among AFP, PSA, CEA, CA19-9, CA125, stomach cancer marker, breast cancer marker, lung cancer marker, and CA15-3. The capture probe may include one to fix glutamine synthetase which is an Alzheimer-specific marker.

The capture probe may include one to fix myoglobin, CK-MB, and troponin I (TnI) that are myocardial infarction markers. The rapid test method may be performing a reaction examination according to immunochromatography method after fixing on the porous membrane one or more markers or capture probes for AIDS, Alzheimer, tumor marker, myocardial infarction, remaining antibiotics, remaining agrichemicals, remaining heavy metals, allergy and breast cancer examination, food poison germ examination (for example, coliforms, salmonellas, etc.). The immunochromatography method is an examination method combining immunochemistry and chromatographic assay, and may include examination methods applying specific immune reactions of an antibody to an antigen, the coloration characteristics and fluidity of colloidal gold, movement of molecules by the capillary phenomenon of a porous membrane.

The immunochromatography method may combine sample dilution, washing and coloration through reaction of an enzyme complex and a substrate that can be seen in the conventional multi-stepped immune measuring method, into one step, thereby enabling quick examination. Also, easiness, economic advantage, and quicker reading of an examination result can be obtained through determining the examination result without using a predetermined device. The immunochromatography method and the rapid test method are well known to the persons skilled in the art.

For the CD and DVD as thin films, a standard CD can be formed, for example, from a 12 cm polycarbonate substrate, a reflection metal layer, and a protection lacquer coating. The format of a CD and a CD-ROM may be described according to an ISO 9660 industry standard. The polycarbonate substrate may be a transparent polycarbonate of an optical quality. A data layer in a CD standard-printed or copied in a large quantity may be part of a polycarbonate substrate and data can be engraved in the form of a series of pits by a stamper in an injection molding process. In this injection molding process, molten polycarbonate is injected into a mold under high pressure, and then cooled down to have a mirror shape such that the polycarbonate can have a mold, stamper or a mirror image of the stamper and pits indicating binary data on a disc substrate can be generated by the polycarbonate substrate. A stamping master may be glass in general. This disc can be modified and remodeled into a thin-film-type analyzer for diagnosing and detecting a small amount of materials in a fluid, such as a thin-film chemical analyzer. In this case, during the injection molding process, channels through which a fluid can flow, chambers capable of storing buffer liquids, holes, and valves can be formed on the disc surface instead of pits. Also, a series of liquid bars for the liquid barcode can be formed by mounting bar-shaped chambers on the disc. The diameter of the disc may be 120 mm, 80 mm, or 32 mm.

The liquid barcode may be suitable as barcodes for a thin-film chemical analyzer for diagnosing and detecting a small amount of bio or chemical materials in a fluid such as a lab-on-a-chip, a protein chip, and a DNA chip. Hereinafter, a disc in which the thin-film chemical analyzer is integrated into a normal disc such as a CD-ROM and DVD will be referred to as a "bio disc".

Also, the liquid barcode may be integrated into a disc such as a normal CD-ROM, and DVD, and a bio disc. The plastic body can be replaced by a variety of materials such as glass, silica and silicon wafer. For example, plastic may be suitable because of economic reasons, easiness of processing, and compatibility with the conventional laser reflection basic detectors such as a CD-ROM and DVD readers. For example, the plastic body can be formed with one or more selected from a group of polypropylene, polyacrylate, polymethyl methacrylate (PMMA), cyclic olefin copolymer (COC), and polycarbonate.

In the liquid barcode reader, the light source of the spectrometer may be a laser module in which a plurality of lasers having different wavelengths are constructed in the form of modules. The lasers may be laser diodes.

The liquid barcode reader may further include: a slider on which the spectrometer is mounted and moving a predetermined position of the spectrometer in a radial direction on the bio disc; a spindle motor rotating the bio disc; and a slide motor controlling the movement of the slider. The slider can move to a radial position of a liquid barcode arranged on the bio disc through a "radial direction movement" of the bio disc. Then, by rotating the bio disc, the liquid barcode can be read by the spectrometer. The "radial direction movement' is a process for moving the spectrometer in the radial direction, and can be performed by moving the slider to a position corresponding to a distance r from the center of the bio disc. By way of a gear link unit of a slide motor or a sled motor, the slider can performed reversible movements from the center of the bio disc to the outer circumference direction or from the outer circumference to the center of the bio disc.

The bio disc may further include a reference hole on a radius of a liquid barcode so that whenever a photo detector detects the reference hole during rotation of the bio disc, a reference trigger signal can be provided to the liquid barcode reader. Hereinafter, a 2-dimensional position on the bio disc will be expressed by a distance r and an angle $\theta$. That is, a position on the bio disc can be expressed by coordinates $(r, \theta)$. For example, the angle $\theta$ may be calculated by taking the reference hole on a zero degree line. Hereinafter, it will be assumed that the start position and the end position of the liquid barcode are $(r_0, \theta_{start})$ and $(r_0, \theta_{end})$, respectively.

In the liquid barcode reader, for example, the spectrometer may first perform "radial direction movement" for moving the liquid barcode to a corresponding radius $r_0$ before reading the liquid barcode on the bio disc. The "radial direction movement" is a process for moving the spectrometer in the radial direction, and can be performed by moving the slider to a position corresponding to the distance $r_0$ from the center of the bio disc. Then, an "azimuthal search" may be needed on the radius $r_0$. The "azimuthal search" may be performed while the bio disc is being rotated. For example, the "azimuthal search" may be performed by obtaining only a signal in a liquid barcode area $(r_0, \theta_{star}-\theta_{end})$ from a detection signal obtained by the spectrometer on the radius $r_0$, with reference to the reference trigger signal and the FG signal, or by obtaining a liquid barcode area by the spectrometer recognizing a quiet zone. The FG signal is explained in a data sheet of Mitsubishi semiconductor M63022FP (Spindle motor and 5ch actuator driver). The FG signal is a frequency signal in proportion to the rotation speed of a motor. In general, the FG signal is obtained by a hall sensor of a motor or an FG sensor, which is well known to persons skilled in the art. The frequency of the FG signal can be increased in proportion to the speed of a motor. Since the pulse interval of the FG signal corresponds to one rotation of the bio disc, i.e., 360 degrees, the liquid barcode area $(\theta_{star}-\theta_{end})$ can be calculated from the reference trigger.

The azimuthal rotation of the bio disc for the "azimuthal search" can be performed by rotation of a step motor geared on a spindle motor.

In the liquid barcode reader, the CPU may recognize a liquid barcode read by the spectrometer, remotely transmit the information of the liquid barcode through the Internet, and receive from a remote server on whether a product is genuine or not, product identification information and product information. The server may be a server of a disc manufacturer or a credit card company. When a product is not genuine, it may be broken down into two cases. It may be a case where a liquid barcode does not exist in the product itself or a case where even though a barcode exists, the barcode does not match. In either case, product identification information from the (remote) server cannot be received, and in that case, the liquid barcode reader sends an error message to the user through a voice unit or display unit.

ADVANTAGEOUS EFFECTS

The liquid barcode according to the embodiments is a thin-film type and cannot be copied. Accordingly, it can be integrated into a normal disc such as a CD-ROM and DVD and a thin-film such as a magnetic card, thereby increasing reliability in authentication and identification of a product. Also, the liquid barcode according to the embodiments can increase the amount of information without a limit compared to the conventional barcodes thanks to the variety of the characteristics of liquids.

EXPLANATION OF MAJOR PARTS OF DRAWINGS

1: TOP SUBSTRATE
2: MIDDLE SUBSTRATE
3: BOTTOM SUBSTRATE
4A, 4B, 4C: VALVE CLOSING UNIT
5A: VALVE OPENING AND CLOSING UNIT
12: EXHAUSTION OUTLET
46: PHOTO DETECTOR
65A: START QUIET ZONE
65B: STOP QUIET ZONE
70A-71D: VALVE
99A: LIGHT SOURCE DEVICE
99B: REFLECTION LAYER
100: BIO DISC
100A: LIQUID BARCODE READER
101: CPU
102: SPINDLE MOTOR
103A: SPECTROMETER
103B: OPTICAL PICKUP DEVICE
104: COMPRESSION UNIT
108A, 108B: SLIDE ARM
109: SLIDE MOTOR
110: MAGNETIC CARD READER
110A: WAFER OR HARNESS
110B: FLEXIBLE CABLE
111: INPUT AND OUTPUT APPARATUS
113: STORAGE DEVICE
120: SAMPLE INJECTION UNIT
121: SAMPLE INJECTION OPENING
130, 131, 132, 133, 140, 141, 143, 150, 151, 152, 153: CHAMBER
132: LIQUID BAR
134: SPACE BAR
140: CIRCUIT BOARD
170: APERTURE
181: TURNTABLE
188: MAGNETIC TAPE

200: LIQUID BARCODE
211: SLIDER
300: MAGNETIC CARD

MODE OF THE INVENTIVE CONCEPT

Exemplary embodiments of the inventive concept will now be described more fully with reference to the accompanying drawings.

Figure 1:
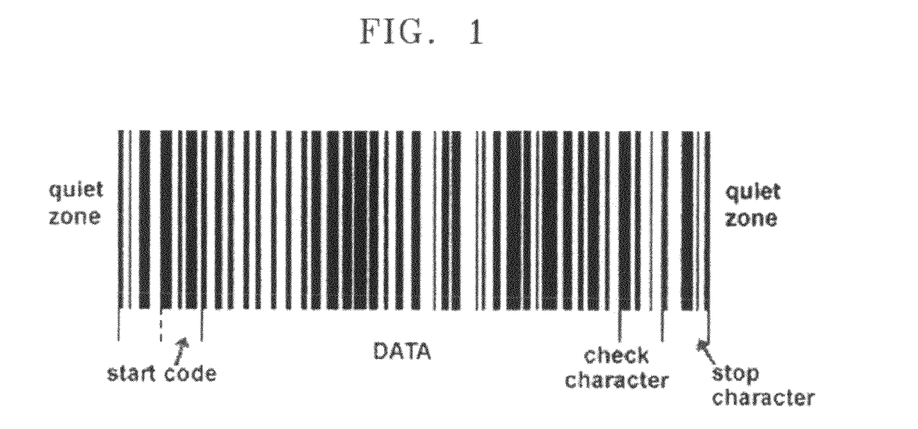
FIG. 1 is a diagram illustrating a conventional barcode system.

FIG. 1 is a diagram illustrating a conventional barcode system. The conventional barcode may comprise a combination of thick or thin bars (black bars) and space bars (white bars) which are formed and arranged to represent alphanumeric characters or special symbols so that those can be easily read. Also, there are about 150 types of barcode systems according to the ratios of the thickness of bars and the widths of spaces. A barcode may be expressed according to each code system and this representation of a barcode in a particular code system is referred to as a barcode symbol. The barcode symbol has blank spaces at the start and end of the barcode. The blank spaces are referred to as quiet zones. The quiet zone is defined to be 10 times or greater than a narrowest element. The quiet zones indicate a blank part before a start character and a blank part after a stop character. The quiet zones are generally essential for implementing clear start and stop of a barcode. The start character is a character recorded at the forefront of the symbol containing portion of the barcode, and can play a role informing a barcode scanner of the input direction of data and the type of barcode. The stop character can indicate that the symbol containing portion of the barcode ends, so that the barcode scanner can read the barcode from either end of the barcode. Also, the barcode may include a check character which is used to check whether or not a message is accurately read. The check character can be used in a field requiring accuracy of information. The barcode symbol may include information called an "interpretation line" on the top or bottom of the barcode that can be visible to human eyes (and may include numbers, characters, symbols, etc.). These lines may include a manufacturer code and product classification code.

Figure 2:
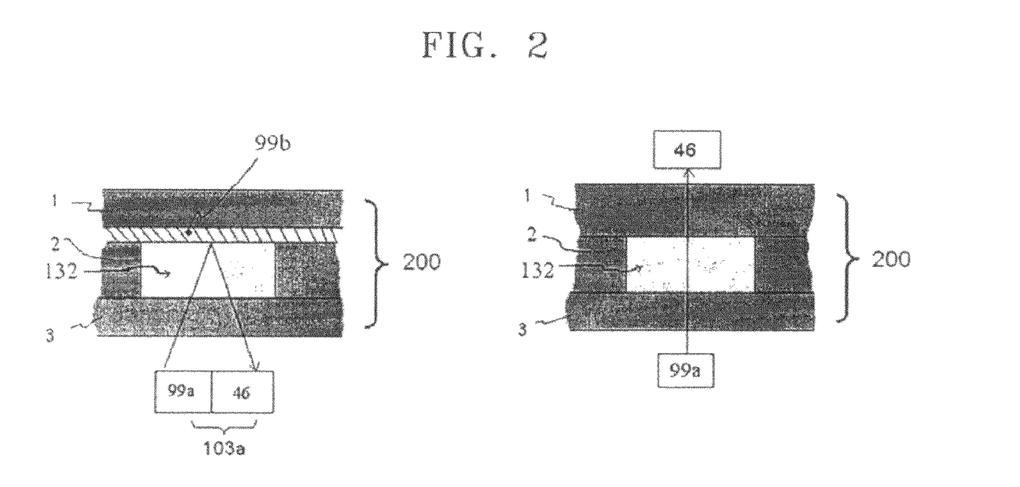
FIG. 2 illustrates a variety of embodiments of liquid bars integrated in a plastic body according to an embodiment of the inventive concept.
Figure 3:
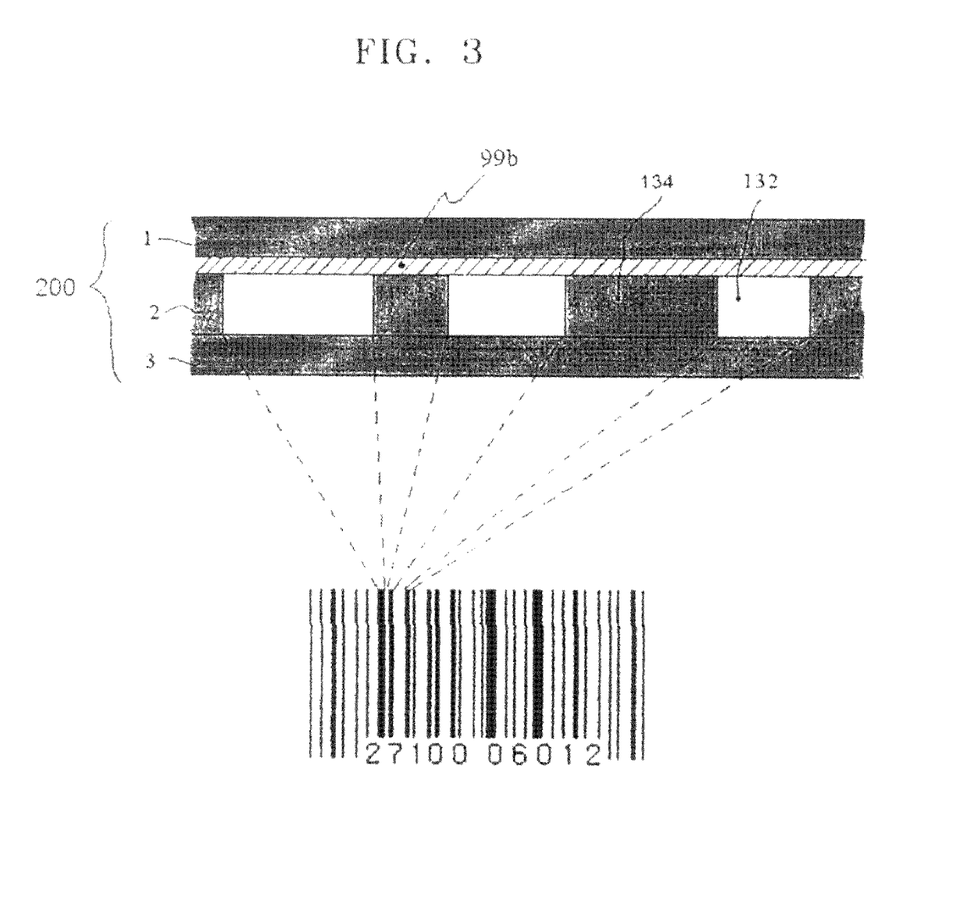
FIG. 3 is a diagram illustrating a liquid barcode integrating liquid bars having reflection layers according to an embodiment of the inventive concept.

FIGS. 2 and 3 illustrate a variety of embodiments of liquid bars 132 integrated in a plastic body according to an embodiment of the inventive concept. The plastic body may be formed with a top substrate 1, a middle substrate 2, and a bottom substrate 3. The middle substrate 2 and the bottom substrate 3 may be manufactured at the same time from one substrate, and in that case, the middle substrate 2 and the bottom substrate 3 do not need to be distinguished for manufacturing. The substrates may form a liquid bar 132 capable of storing a liquid during an injection molding process.

In an embodiment of the inventive concept, the width of the liquid bar, the width of a space bar 134, and the number of bars may comply with a barcode standard. After adhering the middle substrate 2 and the bottom substrate 3 to each other, a liquid can be filled in the liquid bar 132. In this case, the liquid bar 132 can be easily filled by the liquid by use of a capillary technique.

In an embodiment of the inventive concept, the surface of the bottom substrate 3 of the liquid bar 132 may be coated with a hydrophile material. If it is coated with the hydrophile material, it may be easier to fill a liquid in the liquid bar 132. Finally, after filling the liquid, the top substrate is attached, thereby making a liquid barcode 200 formed with a series of liquid bars 132 and space bars 134. For example, in a manufacturing process, in a state in which the middle substrate 2 and the bottom substrate 3 are combined in a laminated manner, a liquid may be injected into the liquid bar 132 in a predetermined quantity by a dispenser (an injection unit to inject a predetermined quantity of a liquid). Then, the top substrate 1 can be combined in a laminated manner.

In an embodiment of the inventive concept, there may be no holes (liquid injection holes) in the top substrate 1 and the bottom substrate 3 forming the liquid barcode 200. This is to prevent liquid evaporation due to incompleteness of sealing of a liquid injection hole. The liquid barcode according to the embodiment does not have a separate liquid injection hole such that evaporation of a liquid can be prevented.

The drawing on the left in FIG. 2 illustrates an embodiment of the inventive concept in which a reflection layer 99B is integrated into the top substrate 1 in the liquid barcode 200 and a spectrometer 103A including a light source device 99A and a photo detector 46 is arranged below the liquid barcode 200. Light of a predetermined wavelength generated by the light source device 99A is passes through the liquid bar 132 and the light reflected on the reflection layer 99B is measured by the photo detector 46, thereby measuring the absorbance amount of the liquid bar 132. The liquid barcode having this reflection layer 99B can be read by a liquid barcode reader in the form of a hand held scanner. Meanwhile, the drawing on the right in FIG. 2 illustrates a liquid barcode without the reflection layer 99B. In this case, the liquid barcode can be read by arranging a light source device 99A at one side of the liquid barcode 200 (shown below the liquid barcode 200 in this example) and arranging a photo detector 46 on the other side of the liquid barcode 200 (shown above the liquid barcode 200 in this example). FIG. 3 is a diagram illustrating a liquid barcode integrating liquid bars having reflection layers 99B as illustrated in the left drawing of FIG. 2 according to an embodiment of the inventive concept.

Figure 4:
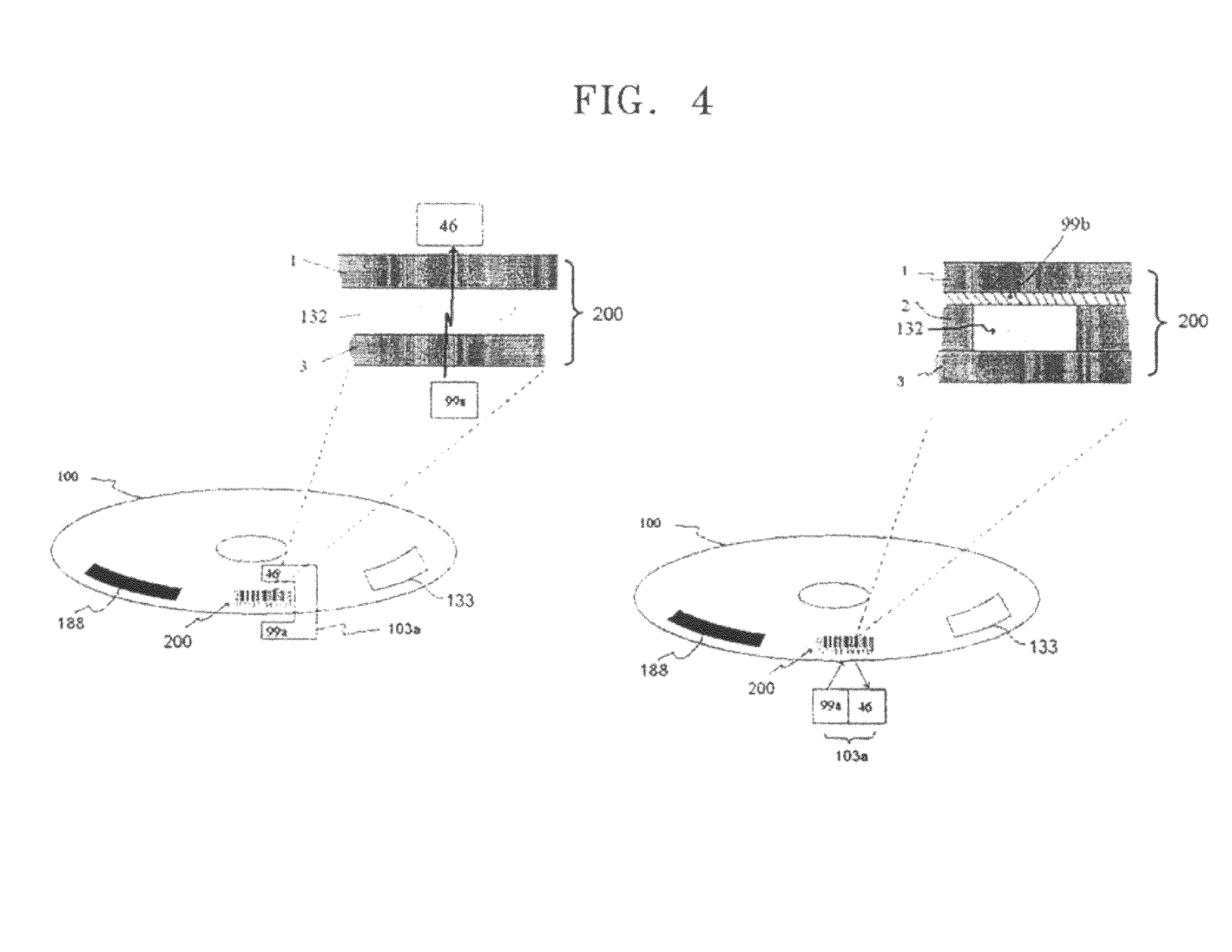
FIG. 4 shows a liquid barcode and a magnetic tape arranged at an outer circumference of a thin-film chemical analyzer according to an embodiment of the inventive concept.

FIG. 4 shows a liquid barcode 200 in which the liquid bars of FIG. 2 are arranged at an outer circumference of the bio disc 100 according to an embodiment of the inventive concept. In this case, a series of liquid bars embedded in the bio disc in the circumference direction can be read by the spectrometer 103A. Here, the light source device 99A selects and outputs light of a predetermined wavelength to each of the liquid bars, and by measuring the absorbance with respect to wavelength, the liquid barcode can be read.

In an embodiment of the inventive concept, for example, a "radial direction movement" and an "azimuthal search" may precede the reading of the liquid barcode by the spectrometer 103A by mounting the spectrometer 103A on a slider 211. The photo detector 46 of the spectrometer may be a CCD image sensor, a CMOS image sensor or a line image sensor.

In an embodiment of the inventive concept, the line image sensor may be a linear sensor array or a contact image sensor (CIS). The spectrometer may further read the reaction result of a biochemical reaction chamber 133 of the bio disc. The biochemical reaction chamber may be a chamber in which a capture probe performing a biological or biochemical reaction with the bio material (sample) or performing a specific binding reaction with the sample is fixed. Reference numeral 188 indicates magnetic tape.

Figure 5:
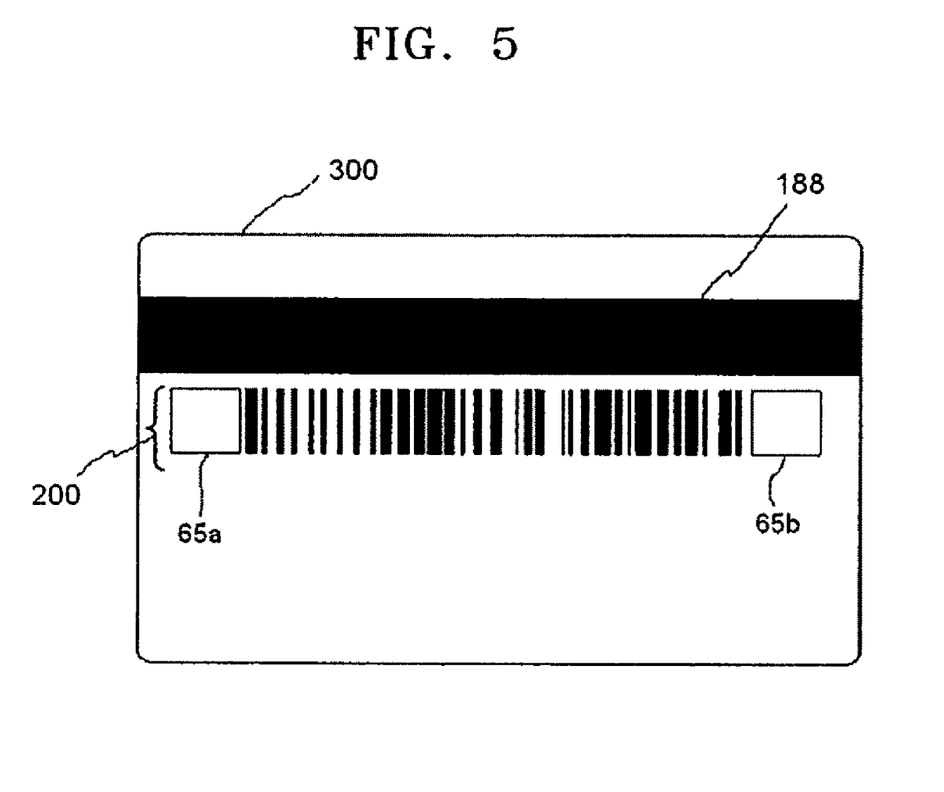
FIG. 5 is a diagram illustrating a liquid barcode arranged in a magnetic card according to an embodiment of the inventive concept.

FIG. 5 is a diagram illustrating a liquid barcode 200 arranged in a magnetic card 300 according to an embodiment of the inventive concept. In this case, while the magnetic tape 188 is read while simultaneously reading the liquid barcode 200, thereby combining or comparing the information of the magnetic tape 188 and the liquid barcode 200 such that the authenticity of the magnetic card 188 can be determined. The magnetic tape 188 and the liquid barcode 200 may store individual encryption information and information required for authentication of a magnetic card, thereby preventing reproduction of the card or preventing others from using the card without permission.

In a liquid barcode reader according to an embodiment of the inventive concept, for example, through reading the liquid barcode 200 on the magnetic card 300 or reading the liquid barcode 200 and the magnetic tape 188, it can recognize whether the plastic body currently loaded on the liquid barcode reader 100A is a genuine credit card.

Reference numbers 65A and 65B indicate a start quiet zone and a stop quiet zone, respectively.

Figure 6:
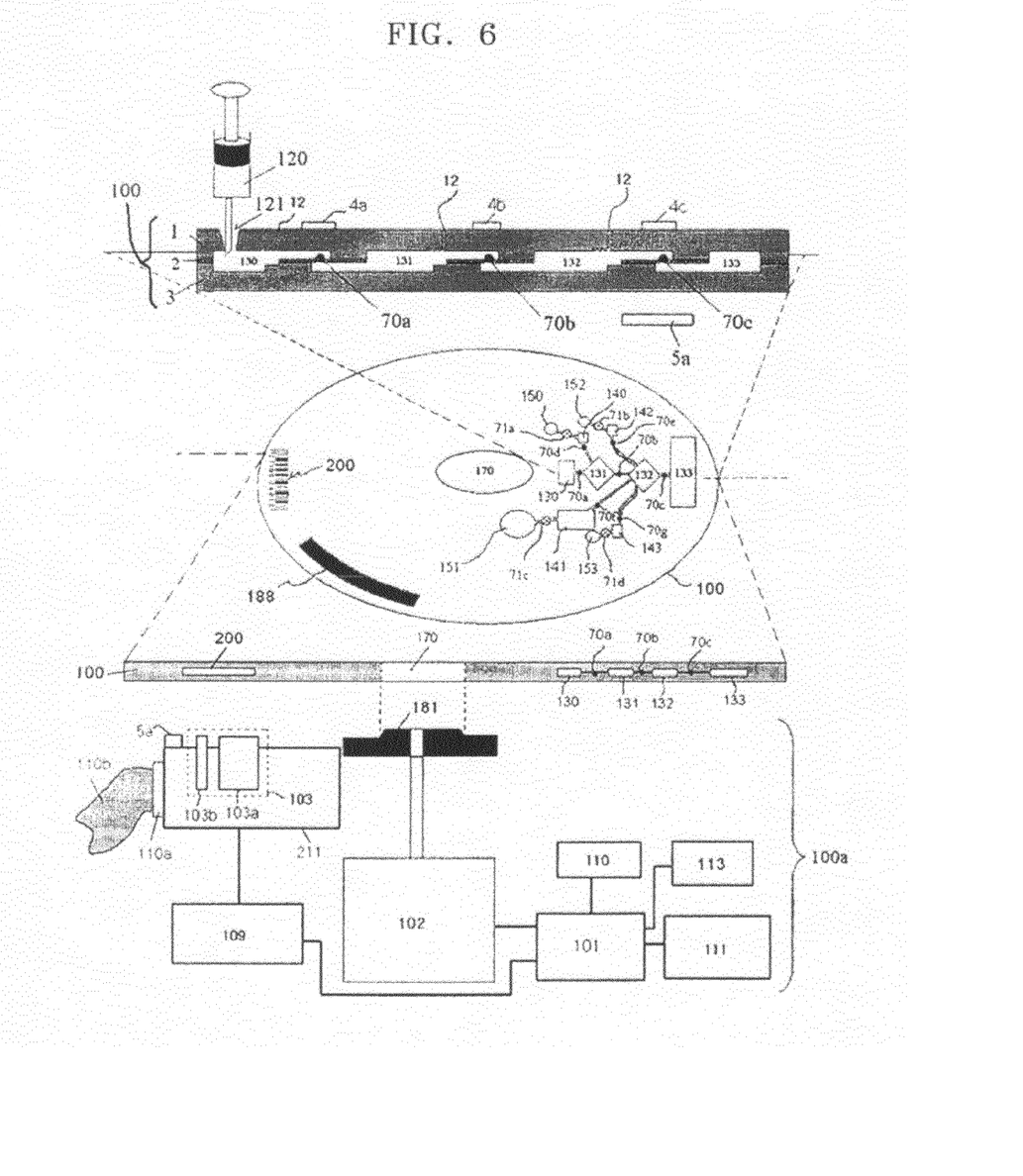
FIG. 6 is a sectional diagram of a liquid barcode reader reading a liquid barcode arranged on a bio disc according to an embodiment of the inventive concept.

FIG. 6 is a sectional diagram of a liquid barcode reader 100A reading a liquid barcode 200 arranged on the bio disc 100 according to an embodiment of the inventive concept. Referring to FIG. 6, in the bio disc 100 the whole process of analysis is integrated on a lab-on-a-chip which is a thin film like a disc generally resembling a normal CD-ROM or DVD. For example, a variety of buffer liquids required for analysis are stored, and chambers 130, 131, 132, 140, 141, 142, 150, 151, 152, and 153 for performing a variety of chemical processes, channels for moving processed fluids and buffer liquids, and valves 70A, 70B, 70C, 70D, 70E, 70F, 70G, 71A, 71B, 71C, and 71D for controlling opening and closing of the channels can be integrated on the bio disc 100. Reference numbers 4A, 4B, and 4C indicate closing units of corresponding valves, and reference number 5A indicates a movable valve closing and opening unit. Reference number 121 indicates an aperture for injecting a sample and reference number 120 indicates a unit for injecting a sample. Reference number 12 indicates an exhaustion outlet. Reference number 211 indicates a slider mounting the spectrometer 103A and the slider 211 can be connected to a slide motor 109 and driven and controlled. The slider 211 can mount the spectrometer 103A for reading the liquid barcode 200 or performing quantitative or qualitative analysis of the biochemical reaction chamber 133, and an optical pickup unit 103B for reproducing (playing) data on a normal optical disc (CD or DVD). Spatial addressing of the biochemical reaction chamber 133 or the liquid barcode 200 on the bio disc 100 is performed by spatially moving the spectrometer 103A to a corresponding position by controlling the slide motor 109. In this case, the spectrometer 103A can read the biochemical reaction chamber 133 and the liquid barcode 200. The radial direction movement can be performed by controlling the slide motor 109. The "azimuthal search" can be performed by rotating the bio disc 100 a predetermined angle by controlling a short rotation or continuous rotations of the spindle motor 102 or controlling a step motor while stopping the slider 211. The step motor may operate with being coupled with gears on the axis of the spindle motor. Reference number 110B indicates a flexible cable for transferring a variety of control signals required for the spectrometer 103A and the optical pickup device 103B on the slider 211, and can be connected to a central processing unit (CPU) 101 through a wafer or harness 110A. Reference number 181 indicates a turntable on which the bio disc 100 is to be placed, and with the central aperture 170 of the disc, the disc can be front or top loaded on the turntable 181.

In an embodiment of the inventive concept, for example, the liquid barcode reader 100A may store the result of reading the liquid barcode 200 or the magnetic tape 188 into a storage device 113, or transmit the result out through an input and output device 111. That is, with the input and output device 111 the CPU 101 provides a communication unit which recognizes a liquid barcode read by the spectrometer, remotely transmits the information of the liquid barcode through the Internet, and receives from a server information on whether a product is genuine or not, product identification information and product information, or authentication information.

In an embodiment of the inventive concept, for example, the input and output device 111 may comply with a communication standard of a universal serial bus (USB), IEEE1394, ATAPI, SCSI, or the Internet communication network. Reference number 110 indicates a magnetic card reader for reading the magnetic tape 188.

Figure 7:
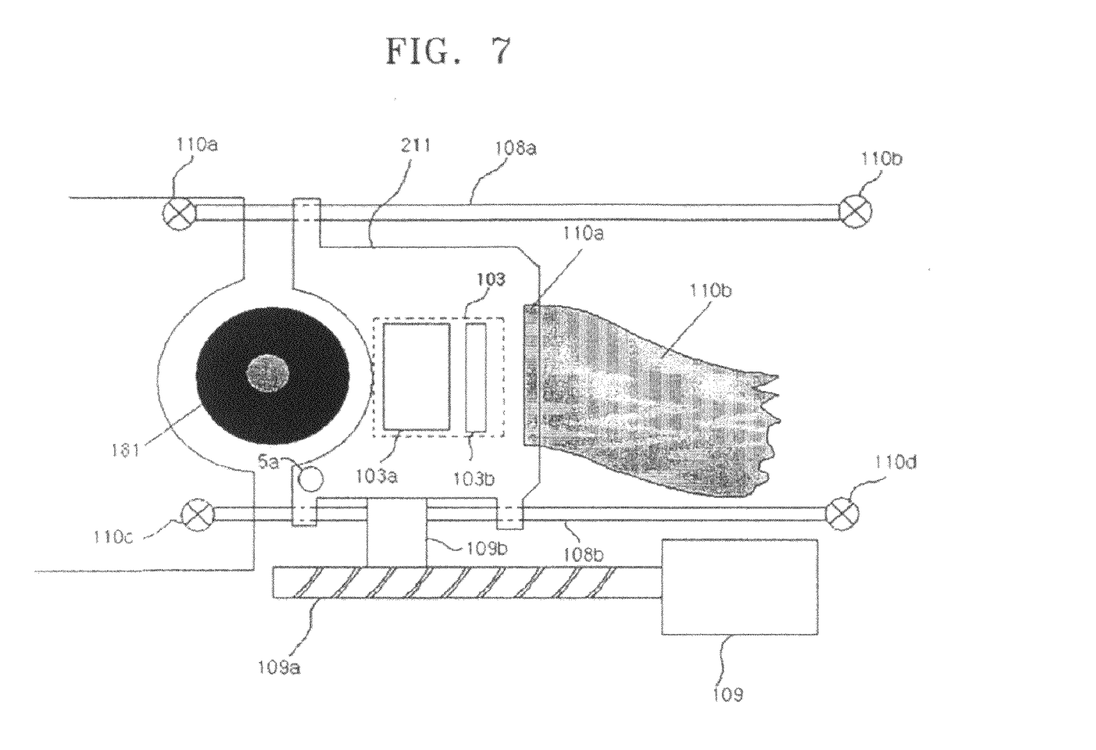
FIG. 7 is a plan view of a slider in which a bio pickup module (BOPM) is installed and arranged according to an embodiment of the inventive concept.

FIG. 7 is a plan view of a slider 211 in which the spectrometer 103A and the optical pickup device 103B are installed and arranged according to an embodiment of the inventive concept. A reversible radial direction movement of the slider 211 centered around the turntable 181 can be controlled by worm gear connection units 109A and 109B connected to the slider motor 109. The slider 211 can be moved in a sliding manner by using slide arms 108A and 108B as guides. The slide arms 108A and 108B can be coupled with the body of the liquid barcode reader 100A through screws 110A, 110B, 110C, and 110D. Reference number 100B indicates a flexible cable, which can be connected using a wafer or harness. Reference number 181 indicates a turntable rotated by the spindle motor 102.

In an embodiment of the inventive concept, the magnetic tape may be arranged after being embedded in the bio disc. In this case, the magnetic tape can be protected from external damage. Reference number 5A indicates the movable valve opening and closing unit that is installed on the slider 211.

Figure 8:
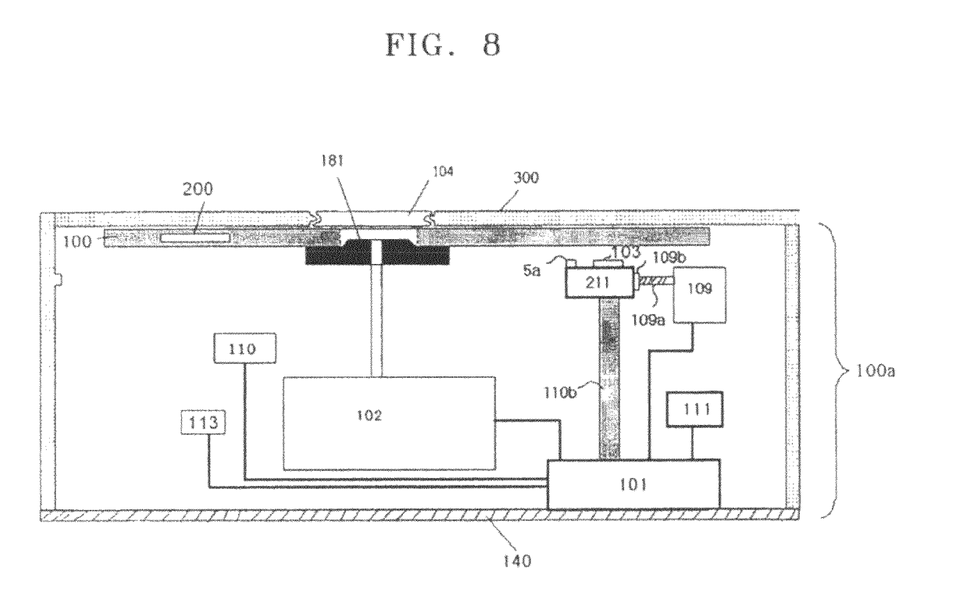
FIG. 8 is a side view of a liquid barcode reader driving and controlling the thin-film chemical analyzer of FIG. 6 according to an embodiment of the inventive concept.

FIG. 8 is a side view of a liquid barcode reader 100A driving and controlling the bio disc 100 illustrated in FIG. 6 according to an embodiment of the inventive concept. Reference number 300 indicates a body supporting the liquid barcode reader 100A. On the bottom of the liquid barcode reader, a circuit board 140 is joined and coupled to the body 300 of the liquid barcode reader 100A. A CPU 101 for controlling the liquid barcode reader 100A, and a storage device 113, or an input and output device 111 are arranged and designed on the circuit board 140. The CPU 101 controls the spindle motor 102 for rotating or stopping the bio disc 100, and in addition, controls the movement of the optical pickup device 103B mounted on the slider 211 through control of the slide motor 109, and can move the position of the spectrometer 103A for reading the liquid barcode 200 and the biochemical reaction chamber 133. Also, the CPU 101 determines whether the disc currently loaded on the liquid barcode reader 100A is a normal optical disc (for example, a music CD, CD-R, game CD, DVD, etc.) or a bio disc 100. If it is a normal optical disc, the CPU 101 performs normal operations of an optical disc, such as transmitting the contents (data) read from the disc to the storage device 113 or the input and output device 111 from the optical pickup device 103B, or transmitting contents (data) to be written to the optical pickup device 103B, and providing a variety of control signals required for read and/or write to individual units. If the disc is a bio disc, the CPU 101 can transmit a variety of control instruction signals for controlling a process of a lab-on-a-chip to the individual units.

In an embodiment of the inventive concept, for example, at the time of loading the bio disc, the barcode reader 100A may read the liquid barcode 200 or the magnetic tape 188 so as to determine validity of the bio disc, product information of a thin-film chemical analyzer, and to perform product authentication of the bio disc.

In an embodiment of the inventive concept, for example, by recognizing a unique identification of the bio disc 100 through reading of the liquid barcode or magnetic tape of the bio disc 100, the CPU 101 may recognize whether or not the disc currently loaded on the liquid barcode reader 100A is a bio disc.

In an embodiment of the inventive concept, for example, the result of reading the liquid barcode 200 or the biochemical reaction chamber 133 may be transmitted to the CPU 101 or the storage device 113 or the input and output device 111 through the flexible cable 110B connected to the slider 211. Reference number 104 indicates a compression unit of the bio disc 100 loaded on the turntable 181, and the compression unit 104 may be designed so as to move in the vertical direction and perform idle rotations. The light source device of the spectrometer outputs a plurality of light wavelengths for measuring transmittance or absorbance, and can make a photo detector measure the transmittance or absorbance of light with respect to a specific wavelength. For example, the spectrometer is formed with a light source, a wavelength selector, a sample container (a test tube or the biochemical reaction chamber 133), and a photo detector, which is well known to persons skilled in the art. The spectrometer can adjust the transmittance to be 100% (zero absorbance) by using a blank solution, and then, can measure the absorbance of a sample solution. The light source may include one that can emit light of a consistent amount having sufficient energy in a wavelength range required for sample analysis. As the light source, a tungsten filament lamp, a hydrogen or deuterium lamp, a white light light-emitting diode (LED), an electronic flash, and a laser can be used. According to an embodiment of the inventive concept, the light source may be a white light LED, an RGB laser, a laser diode (LD) module integrating a plurality of LDs, or an electronic flash. The RGB laser is a device in which three lasers emitting red, green and blue light are formed as one module. By combining these three laser output powers, a light having a variety of wavelengths required in sample analysis can be obtained. The LD module is obtained by modularizing a plurality of LDs having different wavelengths, and by turning on LDs emitting light of predetermined wavelengths in order, the absorbance of a sample with respect to the wavelength can be measured. The wavelengths may be one or more selected from among 340 nm, 405 nm, 450 nm, 505 nm, 546 nm, 570 nm, 600 nm, and 700 nm. At a time when the electronic flash is turned on, the photo detector can measure the absorbance of an object for measuring. The white light LED or the RGB laser or the LD module or the electronic flash can reduce the size of the light source device. If light emitted from the light source is a white light, it is very important for the spectrometer to obtain light of a predetermined wavelength from the light emitted from the light source. In an ideal case, a strict monochromatic radiation is obtained. However, since this is very difficult in reality, the degree of monochromatization of a light showing a wavelength distribution of an arbitrary range can be expressed by specifying the bandwidth of the spectrum. The light closer to a single wavelength of a light source can increase the sensitivity of measurement and resolution. A light having a desired wavelength can be obtained using a wavelength selector. A filter or grating mirror or a combination of them can be used as the wavelength selector. The grating mirror can play the role of a kind of prism reflecting an incident light in a dispersed manner.

Figure 9:
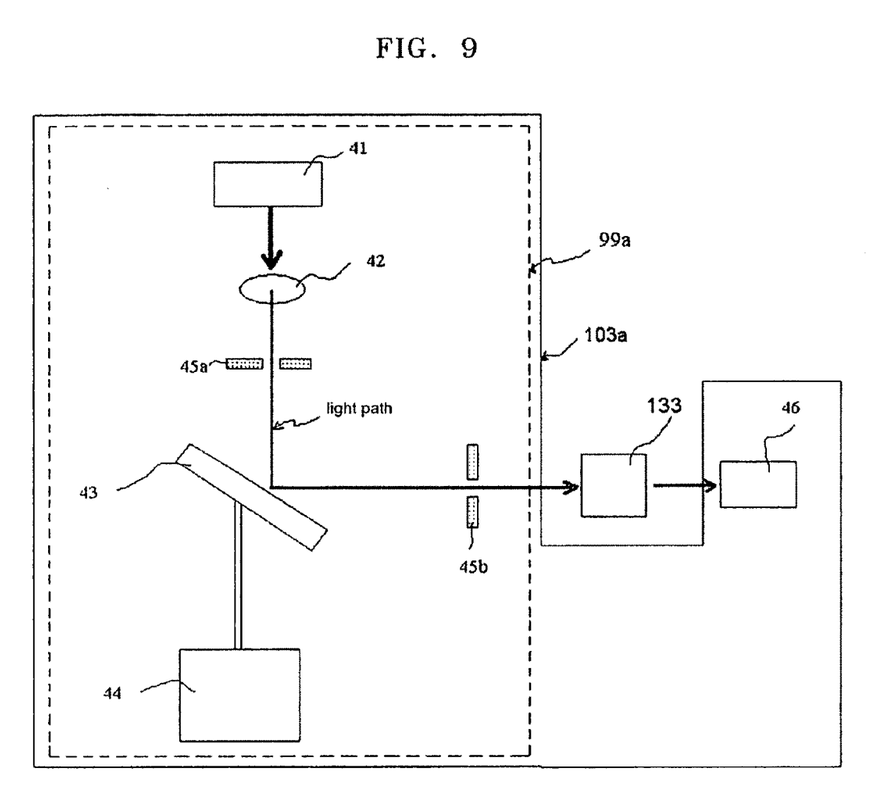
FIG. 9 shows a spectrometer using a grating mirror according to an embodiment of the inventive concept.

FIG. 9 shows a spectrometer 108 (not shown) using a grating mirror according to an embodiment of the inventive concept. The spectrometer 108 may be formed by a light source device 99A and a photo detector 46. Referring to FIG. 9, white light from the light source 41 is focused by a lens 42 to generate a beam, and then, the beam is passed through a first H-slit and V-slit 45A, thereby generating a spot beam. If the spot beams are made to be incident on the grating mirror 43, the light reflected on the grating mirror 43 can be separated in a phase space with respect to wavelength. A second H-slit and V-slit 45B is fixed and arranged in a predetermined angle so that only a light having a predetermined wavelength can be obtained from among the light separated in the phase space after reflection on the grating mirror 43. In this case, by rotating the grating mirror 43 using the step motor 44, the wavelength of the light passing the second H-slit and V-slit 45B can be adjusted. That is, by controlling the rotation angle of the grating mirror 43, light of a desired predetermined wavelength area can be obtained from the outlet of the second H-slit and V-slit 45B as the light passes therethrough. The thus obtained light having a predetermined wavelength is passed through a biochemical reaction chamber 133 and a liquid bar 132, and then, the photo detector 46 measures this light. By doing so, the absorbance or transmittance amount or the intensity of color is measured, and the optical characteristics of the liquid can be quantitatively analyzed. As the qualitative or quantitative analysis methods of the biochemical reaction chamber 133 using the spectrometer, methods such as an end point method, a rate assay method, and an initial rate method which are well known to the persons skilled in the art can be used. Reference number 41 indicates the light source of the spectrometer 108. The wavelength selector can be formed with the step motor 44 for controlling the rotation angle of the grating mirror 43, the lens 42 for focusing the light from the light source, the first H-slit and V-slit 45A for generating a spot beam from the focused beam, the grating mirror 43 for separating the spot beam with respect to wavelengths, and the second H-slit and V-slit 45B for passing only a beam of a predetermined angle reflected from the grating mirror 43 (i.e. light having a predetermined wavelength). The light having a predetermined wavelength obtained by the light source 41 and the wavelength selector is passed through the biochemical reaction chamber 133 or the liquid bar 132, and the photo detector 46 measures the absorbance amount of the light. By doing so, the chemical reaction result of the biochemical reaction chamber 133 can be qualitatively or quantitatively analyzed or the liquid barcode can be read. By rotating the step motor 44, light of various wavelengths can pass through the biochemical reaction chamber 133 or the liquid bar 132, and the absorbance amounts of the light can be measured with respect to wavelength.

In an embodiment of the inventive concept, optical fiber may be used instead of the first H-slit and V-slit or the second H-slit and V-slit. Hereinafter, a combination of the light source 41, the lens 42, the first H-slit and V-slit 45A, the grating mirror 43, and the second H-slit and V-slit 45B will be referred to as a light source device 99A. The LD module and RGB module may form the light source device 99A, and in that case, the light source device 99A can be simplified. The liquid bar of the quiet zones 65A and 65B may store a blank solution. After the spectrometer is adjusted so as to make the transmittance of the blank solution 100% (zero absorbance), the absorbance of a liquid inside a liquid bar in a data area can be measured. While the bio disc is rotated, by setting the absorbance of a blank solution to always be "0" and based on the fact that the quiet zones 65A and 65B each have a width ten times wider than a narrowest element, the quiet zones 65A and 65B can be recognized and accordingly, the start and end of the liquid barcode can be identified. Accordingly, while the bio disc is rotated, spatial addressing and reading of a liquid barcode is also possible. Also, for example, by making the widths of the start quiet zone 65A and the stop quiet zone 65B different from each other, they can be distinguished from each other.

In a liquid barcode reader according to an embodiment of the inventive concept, for example, the CPU 101 may recognize information of the read liquid barcode or magnetic tape, and if it is determined that a normal optical disc (a CD and a DVD) or a unusable bio disc is loaded, may eject the disc from the liquid barcode reader or send a warning message to a user. Also, in the magnetic tape, information on whether the disc is a bio disc previously used several times, or validity period information, or types of disease desired to be diagnosed may be stored. That is, when a throwaway bio disc is ejected in the middle of being used or after completion of use, the history is recorded in the magnetic tape. If the bio disc is loaded later, the user can be informed that the bio disc cannot be used for diagnosis. Also, according to the validity period information, if a bio disc whose validity period is over is loaded, the user can be informed that the bio disc cannot be used for diagnosis.

While the inventive concept has been particularly shown and described with reference to exemplary embodiments thereof, it will be understood by those of ordinary skill in the art that various changes in form and details may be made therein without departing from the spirit and scope of the inventive concept as defined by the following claims. The exemplary embodiments should be considered in descriptive sense only and not for purposes of limitation. Therefore, the scope of the inventive concept is defined not by the detailed description of the inventive concept but by the appended claims, and all differences within the scope will be construed as being included in the present inventive concept.

The invention claimed is:

1. A liquid barcode comprising:

liquid bars formed of bar-shaped chambers filled with liquid;

space bars formed in the gaps between the liquid bars; and a plastic body formed by arranging in parallel and integrating therein a plurality of the liquid bars and space bars, wherein the plastic body selectively further comprises a magnetic tape.

2. The liquid barcode of claim 1, wherein the liquid bar of a quiet zone of the liquid barcode stores a blank solution.

3. The liquid barcode of claim 1, wherein the liquid bar is formed with liquid including nanoparticles of different sizes, or different densities, or different 3-dimensional structures.

4. The liquid barcode of claim 1, wherein the plastic body further comprises a reflection layer.

5. The liquid barcode of claim 1, wherein the plastic body is integrated on a magnetic card, a bio disc, or a thin-film chemical analyzer.

6. A liquid barcode reader comprising:

a spectrometer reading optical characteristics of a liquid barcode selected from among the group of barcodes of claims 1, 2, and 5; and a central processing unit (CPU) controlling the spectrometer, and/or driving a bio disc or a thin-film chemical analyzer.

7. The liquid barcode reader of claim 6, wherein a light source of the spectrometer is any one selected from among a white light light-emitting diode (LED), a RGB laser, an LD (laser diode) module, and an electronic flash.

8. The liquid barcode reader of claim 6, further comprising a slit allowing the plastic body to enter therein and exit therefrom.

9. The liquid barcode reader of claim 6, further comprising a magnetic card reader reading information of the magnetic tape which can be included in the plastic body.

10. The liquid barcode reader of claim 6, further comprising:
- a slider on which the spectrometer is mounted, moving a predetermined position of the spectrometer in a radial direction on the bio disc;
- a spindle motor rotating the bio disc; and
- a slide motor controlling the movement of the slider.

11. The liquid barcode reader of claim 10, wherein an optical pickup device is further mounted on the slider.

12. The liquid barcode reader of claim 10, wherein the spectrometer first performs the radial direction movement by the slider and then azimuthal search before reading a liquid barcode on the bio disc.

13. The liquid barcode reader of claim 12, wherein the azimuthal search is performed by taking a signal in a liquid barcode area from a detection signal obtained from the spectrometer with reference to a reference trigger signal and a FG (frequency generator) signal while the bio disc rotates, or by taking a signal in a liquid barcode area from a detection signal obtained from the spectrometer with reference to a quiet zone.

14. The liquid barcode reader of claim 12, wherein the azimuthal search is performed by recognizing a quiet zone by using information that the absorbance of a quiet zone is always "0" when a bio disk is rotating and has a width ten times wider than that of a narrowest element.

15. The liquid barcode reader of claim 6, wherein the CPU further comprises an input and output apparatus providing a communication unit which recognizes a liquid barcode read by the spectrometer, remotely transmits the information of the liquid barcode, and receives information on whether a product is genuine or not, product identification information and product information, and/or authentication information from a remote server.

16. The liquid barcode reader of claim 6, wherein the CPU recognizes information of the liquid barcode or magnetic tape, and if it is determined that a normal optical disc (a compact disc (CD), a digital versatile disc (DVD)) or a unusable bio disc is loaded, ejects the disc or sends a warning message to a user.

17. The liquid barcode reader of claim 6, wherein the CPU recognizes information of the liquid barcode or magnetic tape read from the loaded bio disc, and if it is determined that the bio disc is one that was used in the past, ejects the disc or sends a warning message to a user.

18. The liquid barcode reader of claim 6, wherein the CPU recognizes information of the liquid barcode or magnetic tape read from the loaded bio disc, and if it is determined that the validity period of the bio disc is over, ejects the disc or sends a warning message to a user.

19. The liquid barcode reader of claim 6, wherein through reading of the liquid barcode, or the liquid barcode and the magnetic tape on a credit card, it is recognized that the credit card is genuine.

20. The liquid barcode reader of claim 11, wherein the CPU determines whether the disc loaded on the liquid barcode reader is a normal optical disc or a bio disc, and if the disc is a normal optical disc, the CPU performs normal operations for an optical disc, including transmitting data read from the disc by the optical pickup device to a storage device or an input and output apparatus, or transmitting data to be written to the optical disc, and providing a variety of control signals required for reproducing or recording to the optical pickup device, and if the disc is a bio disc, the CPU provides a variety of control instruction signals for controlling processes of a lab-on-a-chip to the spindle motor, the slide motor and the spectrometer.

21. The liquid barcode reader of claim 10, wherein the spectrometer further reads the reaction result of a biochemical reaction chamber in the bio disc.

* * * * *

UNITED STATES PATENT AND TRADEMARK OFFICE
CERTIFICATE OF CORRECTION

PATENT NO. : 8,267,318 B2  
APPLICATION NO. : 12/734262  
DATED : September 18, 2012  
INVENTOR(S) : Jae Chern Yoo Page 1 of 1

It is certified that error appears in the above-identified patent and that said Letters Patent is hereby corrected as shown below:

Title Page, Item (73) (Assignee); Line 1; Delete "Samsung Electronic Co.," and insert -- Samsung Electronics Co., --, therefor.

Signed and Sealed this  
Fourteenth Day of May, 2013

Teresa Stanek Rea  
*Acting Director of the United States Patent and Trademark Office*